(12) United States Patent
Rinott et al.

(10) Patent No.: US 10,677,866 B1
(45) Date of Patent: Jun. 9, 2020

(54) SYSTEMS AND METHODS FOR CORRECTING MEASUREMENT ARTIFACTS IN MR THERMOMETRY

(71) Applicants: Shahar Rinott, Haifa (IL); Yoav Levy, Hinanit (IL)

(72) Inventors: Shahar Rinott, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 0 days.

(21) Appl. No.: 16/202,558

(22) Filed: Nov. 28, 2018

(51) Int. Cl.
*G01R 33/48* (2006.01)
*G01R 33/54* (2006.01)

(52) U.S. Cl.
CPC ......... *G01R 33/4804* (2013.01); *G01R 33/54* (2013.01)

(58) Field of Classification Search
CPC .............................. G01R 33/4804; G01R 33/54
USPC .................................... 324/309, 315; 607/88
See application file for complete search history.

(56) References Cited

U.S. PATENT DOCUMENTS 8,915,948 B2 * 12/2014 Altshuler ................. A61N 1/36
607/88

* cited by examiner

*Primary Examiner* — Farhana A Hoque
(74) *Attorney, Agent, or Firm* — Morgan, Lewis & Bockius LLP

(57) ABSTRACT

Systems and methods for performing magnetic resonance (MR) thermometry include a magnetic resonance imaging (MRI) unit and a controller in communication with the MRI unit and configured to cause the MRI unit to acquire one or more baseline phase images of an imaging region and one or more treatment phase images of the imaging region subsequent to a temperature change of a subregion within the imaging region, electronically generate a thermal map pixelwise indicating the temperature change of the subregion based at least in part on the acquired baseline phase image and treatment phase image, computationally predict the temperature change of the subregion based at least in part on energy deposited in the subregion during treatment without reference to the generated thermal map, and determine whether the thermal map is inaccurate based at least in part on the temperature change of the subregion indicated by the thermal map and the predicted temperature change of the subregion.

21 Claims, 11 Drawing Sheets

SYSTEMS AND METHODS FOR CORRECTING MEASUREMENT ARTIFACTS IN MR THERMOMETRY

TECHNICAL FIELD

The present invention relates generally to magnetic resonance (MR) imaging, and more particularly, to techniques for MR thermal imaging (or MR thermometry) and corrections in MR thermometry.

BACKGROUND

MR imaging of internal body tissues may be used for numerous medical procedures, including diagnosis and surgery. In general terms, MR imaging starts by placing a subject in a relatively uniform, static magnetic field. The static magnetic field causes hydrogen nuclei spins to align and precess about the general direction of the magnetic field. Radio frequency (RF) magnetic field pulses are then superimposed on the static magnetic field to cause some of the aligned spins to alternate between a temporary high-energy non-aligned state and the aligned state, thereby inducing an RF response signal, called the MR echo or MR response signal. It is known that different tissues in the subject produce different MR response signals, and this property can be used to create contrast in an MR image. An RF receiver detects the duration, strength, and source location of the MR response signals, and such data are then processed to generate tomographic or three-dimensional images.

MR imaging can also be used effectively during a medical procedure to assist in locating and guiding medical instruments. For example, a medical procedure can be performed on a patient using medical instruments while the patient is in an MRI machine. The medical instruments may be for insertion into a patient or they may be used externally but still have a therapeutic or diagnostic effect. For instance, the medical instrument may be an ultrasonic device, which is disposed outside a patient's body and focuses ultrasonic energy to ablate or necrose tissue or other material on or within the patient's body. The MRI machine preferably produces images at a high rate so that the location of the instrument (or the focus of its effects) relative to the patient may be monitored in real-time (or substantially in real-time).

MR imaging can further provide a non-invasive means of quantitatively monitoring in vivo temperatures. This is particularly useful in the above-mentioned MR-guided focused ultrasound (MRgFUS) treatment or other MR-guided thermal therapy where temperature of a treatment area should be continuously monitored in order to assess the progress of treatment and correct for local differences in heat conduction and energy absorption. The monitoring (e.g., measurement and/or mapping) of temperature with MR imaging is generally referred to as MR thermometry or MR thermal imaging.

Among various methods available for MR thermometry, the proton-resonance frequency (PRF) shift method is often preferred due to its excellent linearity with respect to temperature change, near-independence from tissue type, and the high spatial and temporal resolution of temperature maps obtained therewith. The PRF shift method is based on the phenomenon that the MR resonance frequency of protons in water molecules changes linearly with temperature (with a constant of proportionality that, advantageously, is relatively constant among tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change, thereby capturing a small phase change that is proportional to the change in temperature.

A phase image, for example, may be computed from MR image data, and a temperature-difference map relative to the baseline image may be obtained by (i) determining, on a pixel-by-pixel basis, phase differences between the phase image corresponding to the baseline and the phase image corresponding to a subsequently obtained MR image, and (ii) converting the phase differences into temperature differences based on the PRP temperature dependence while taking into account imaging parameters such as the strength of the static magnetic field and echo time (TE). It should be appreciated that, although a subtraction step may be involved, the determination of the phase differences involves more than a simple subtraction of scalars.

Unfortunately, changes in phase images do not arise uniquely from temperature changes. Various factors unrelated to temperature, such as changes in a local magnetic field due to nearby moving objects, magnetic susceptibility changes in a patient's body due to breathing or other movements, and magnet or shim drifts can all lead to confounding phase shifts that may render a phase-sensitive temperature measurement invalid. For example, during MRgFUS treatment procedures, one or more treatment devices may need to be re-positioned and/or re-oriented in or near the MR imaging area. Since the treatment devices typically include metal components, their movements could perturb local magnetic fields and thereby significantly change the phase background. Non-metal objects and their movements may also perturb local magnetic fields. For example, the patient's breathing or turning motions could have similar effects on the MR imaging data. In fact, the changes in the magnetic field associated with patient motion and/or nearby objects can be severe enough to render temperature measurements made using the above-mentioned phase-sensitive approach useless.

To detect phase changes resulting from factors unrelated to temperature, various conventional approaches, upon acquiring the MR imaging data, create real-space pixel images of the MR imaging data and identify artifacts appearing in the pixel images. Based on the detected artifacts, phase changes resulting from the non-temperature-related factors are indirectly inferred. Artifacts that have little effect on the pixel images, however, may have significant effects on the phase images. As a result, conventional approaches may still generate flawed thermal maps, which can compromise medical treatment.

Accordingly, there is a need to accurately and reliably identify erroneous MR thermal maps resulting from factors unrelated to temperature so as to ensure an efficient and safe medical procedure.

SUMMARY

Various embodiments of the present invention provide systems and methods for detecting inaccurate temperature maps generated from MR imaging data. For ease of reference, the following description refers to MR imaging data acquired during ultrasound thermal treatment; it should be understood, however, that the same approaches generally apply as well to any MR-guided medical procedures (including diagnosis and surgery) that require continuous temperature monitoring of a region of interest, e.g., for assessing the progress of a procedure.

In some embodiments, prior to the thermal treatment, MR raw imaging data is acquired; the raw data is then processed to identify the location and/or orientation of the target region and generate a baseline phase image. The MR imaging data may be acquired again during thermal treatment and processed to identify the location of the target tissue and generate a treatment phase image. The treatment phase image may then be compared against the baseline phase image acquired prior to treatment, on a pixel-by-pixel basis, to compute the phase differences therebetween; based on the computed phase differences, an MR thermal map indicating the pointwise changes in temperature measured by the MR imaging data can be created. In various embodiments, some or all of the measured, pixel-by-pixel temperature changes in the thermal map are compared against temperature changes predicted using a physical model (again on a pixel-by-pixel basis); based on the deviation between the measured and predicted temperature changes, the accuracy of the acquired thermal map can be determined. For example, if the deviation exceeds a predetermined threshold amount (for individual pixels or over a region of pixels, e.g., on an aggregated basis), the acquired thermal map may be identified as inaccurate. As a result, the acquired thermal map may be discarded, and in some embodiments, ultrasound treatment may be suspended until an accurate thermal map is obtained so as to avoid damage to non-target tissue.

The physical model may computationally predict the change in temperature resulting from the thermal treatment based on, for example, the acoustic energy deposited in the target and/or non-target regions and tissue characteristics, such as anatomic characteristics (e.g., the type, property, structure, thickness, density, etc.) and/or material characteristics (e.g., the speed of sound), of the target and/or non-target regions. The acoustic energy deposited in the target and/or non-target regions may be estimated based on ultrasound parameter values that generate a focal zone at the target region and tissue characteristics of the intervening tissue located on the beam path between the transducer and the target region. In one implementation, the tissue characteristics of the target tissue and non-target tissue (including the intervening tissue and tissue surrounding the target region) are acquired using an imaging device, such as the MRI apparatus, a computer tomography (CT) device, a positron emission tomography (PET) device, a single-photon emission computed tomography (SPECT) device, or an ultrasonography device. In addition, the physical model may further take the form of (or include) differential equations (such as the Pennes model and a bioheat equation) to simulate heat transfer in tissue, thereby predicting the temperature increase in the target/non-target regions during the time interval.

Alternatively or additionally, the temperature increase resulting from thermal treatment may be predicted using a statistical model. For example, the statistical model may include historical data of the accumulated acoustic energy or temperature increase measured during previous thermal treatments performed on the same or different patient. Based on the retrospective study, a statistical model relating the transmitted acoustic power and tissue characteristics to the accumulated acoustic energy or temperature change at the target/non-target regions may be established. Tissue characteristics of the current patient and the ultrasound parameter values employed in the current treatment may then be applied to the statistical model to predict the accumulated acoustic energy or temperature increase during the treatment at a given time or within a time interval.

The predetermined threshold(s) for deciding whether the temperature increase in a thermal map results from a tissue response to the thermal treatment or some extraneous artifacts may be fixed or dynamically varied. For example, the size of the threshold may positively correlate to the amount of acoustic energy transmitted to the target region, so that the threshold is small for small acoustic energies and larger for larger acoustic energies. As a result, at a higher acoustic energy, a larger discrepancy between the measured and predicted temperatures is required to conclude that the measured thermal map is inaccurate. In one embodiment, the predetermined threshold values are adjusted based on the noise level of the acquired MR imaging data. For example, MR imaging data having a smaller signal-to-noise ratio may correspond to a larger threshold value compared with MR imaging data having a larger signal-to-noise ratio. Thus, when the thermal map includes a higher noise level, the measured temperature in a thermal map may have a larger deviation from the predicted temperature before determining that the measured thermal map is flawed.

Predicting the change in temperature during thermal treatment may not be necessary in order to detect inaccurate thermal maps. In some embodiments, detection of the inaccurate map is based on historical imaging data acquired during thermal treatment only. For example, assuming that the transmitted ultrasound power remains constant during treatment, the energy accumulated (and the resulting temperature) at the target region may be expected to increase gradually with time. Thus, if the target or non-target region in a particular temperature map exhibits an abrupt increase or decrease in temperature (e.g., compared with the average increase or decrease for the same region over the previous few images), the temperature map is likely incorrect at the noted region.

Accordingly, various embodiments provide approaches for monitoring in vivo temperatures of the target and/or non-target tissues during thermal treatment and detecting inaccurate thermal maps in real time. This is particularly useful in MR-guided thermal therapy, so that the temperatures of the target and/or non-target tissues can be continuously monitored to assess the progress of thermal treatment and correct for local differences in heat conduction and energy absorption, thereby achieving desired treatment effects at the target and avoiding damage to the non-target tissue.

Accordingly, in one aspect, the invention pertains to a system for performing magnetic resonance (MR) thermometry. In various embodiments, the system includes a magnetic resonance imaging (MRI) unit and a controller in communication with the MRI unit; the controller is configured to (i) cause the MRI unit to acquire one or more baseline phase images of an imaging region and one or more treatment phase images of the imaging region subsequent to a temperature change of a subregion within the imaging region; (ii) electronically generate a thermal map pixelwise indicating the temperature change of the subregion based at least in part on the acquired baseline phase image(s) and treatment phase image(s); (iii) computationally predict, without reference to the generated thermal map, the temperature change of the subregion based at least in part on energy deposited in the subregion during treatment; and (iv) determine whether the thermal map is inaccurate based at least in part on the temperature change of the subregion indicated by the thermal map and the predicted temperature change of the subregion.

The controller may be further configured to compare the temperature change in the generated thermal map against the predicted temperature change so as to determine a deviation therebetween; and compare the deviation against a predetermined threshold. In addition, the controller may be further configured to determine that the thermal map is inaccurate upon determining that the deviation exceeds the predetermined threshold (which may or may not be fixed value). In some embodiments, the controller is further configured to adjust the predetermined threshold based at least in part on the energy deposited in the subregion, the noise level(s) associated with the baseline phase image(s) and/or treatment phase image(s) or the deviation between the temperature change in the generated thermal map and the predicted temperature change.

In one embodiment, the further includes a medical device configured to cause the temperature change of the subregion. For example, the medical device may include an ultrasound transducer having multiple transducer elements. The controller may be further configured to computationally predict the temperature change of the subregion using a physical model. In one implementation, the physical model is based at least in part on the values of ultrasound parameters (e.g., the amplitudes, frequencies, phases, directions or activation times associated with the transducer elements) for generating a focal zone at the subregion.

In various embodiments, the controller is further configured to computationally predict, without reference to the generated thermal map, the temperature change of the subregion using the physical model. The physical model may be based at least in part on the tissue characteristic (e.g., a type, a structure, a thickness, a density, a speed of sound, a thermal absorption coefficient, a perfusion coefficient and/or a metabolic heat generation rate) associated with the subregion and/or the second subregion different from the subregion. In one implementation, the controller is further configured to acquire the tissue characteristic based at least in part on imaging data acquired using the MRI unit. In addition, the physical model may be based on a bioheat transfer equation (e.g., the Pennes equation).

The controller may be further configured to predict the temperature change of the subregion using a statistical model. In addition, the system may further include a medical device configured to cause the temperature change of the subregion; the statistical model may then include historical data of the change in temperature resulting from previous activation of the medical device. In one embodiment, the controller is further configured to cause the MRI unit to acquire a reference library including multiple baseline phase images of the imaging region, each corresponding to a phase background during a different stage of an anticipated motion of the imaging region. The controller may be then further configured to identify a baseline phase image in the reference library that best matches the treatment phase image based on similarity therebetween and generate the thermal map based at least in part on the identified best-matching baseline phase image.

In another aspect, the invention relates to a method of performing MR thermometry. In various embodiments, the method includes acquiring one or more baseline phase images of an imaging region and one or more treatment phase images of the imaging region subsequent to a temperature change of a subregion within the imaging region; electronically generating a thermal map pixelwise indicating the temperature change of the subregion based at least in part on the acquired baseline phase image(s) and treatment phase image(s); computationally predicting, without reference to the generated thermal map, the temperature change of the subregion based at least in part on energy deposited in the subregion during treatment; and determining whether the thermal map is inaccurate based at least in part on the temperature change of the subregion indicated by the thermal map and the predicted temperature change of the subregion.

Another aspect of the invention relates to a system for performing MR thermometry. In various embodiments, the system includes an MRI unit and a controller in communication with the MRI unit; the controller is configured to (i) cause the MRI unit to acquire one or more baseline phase images of an imaging region and multiple treatment phase images of the imaging region subsequent to at least a temperature change of a subregion within the imaging region; (ii) electronically generate multiple thermal maps based at least in part on the acquired baseline phase image(s) and the treatment phase images, each thermal map pixelwise indicating the temperature change of the subregion associated with one of the treatment phase images; and (iii) determine whether one of the thermal maps is inaccurate based at least in part on a comparison between the temperature change associated therewith and the temperature change associated with at least another one of the thermal maps.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
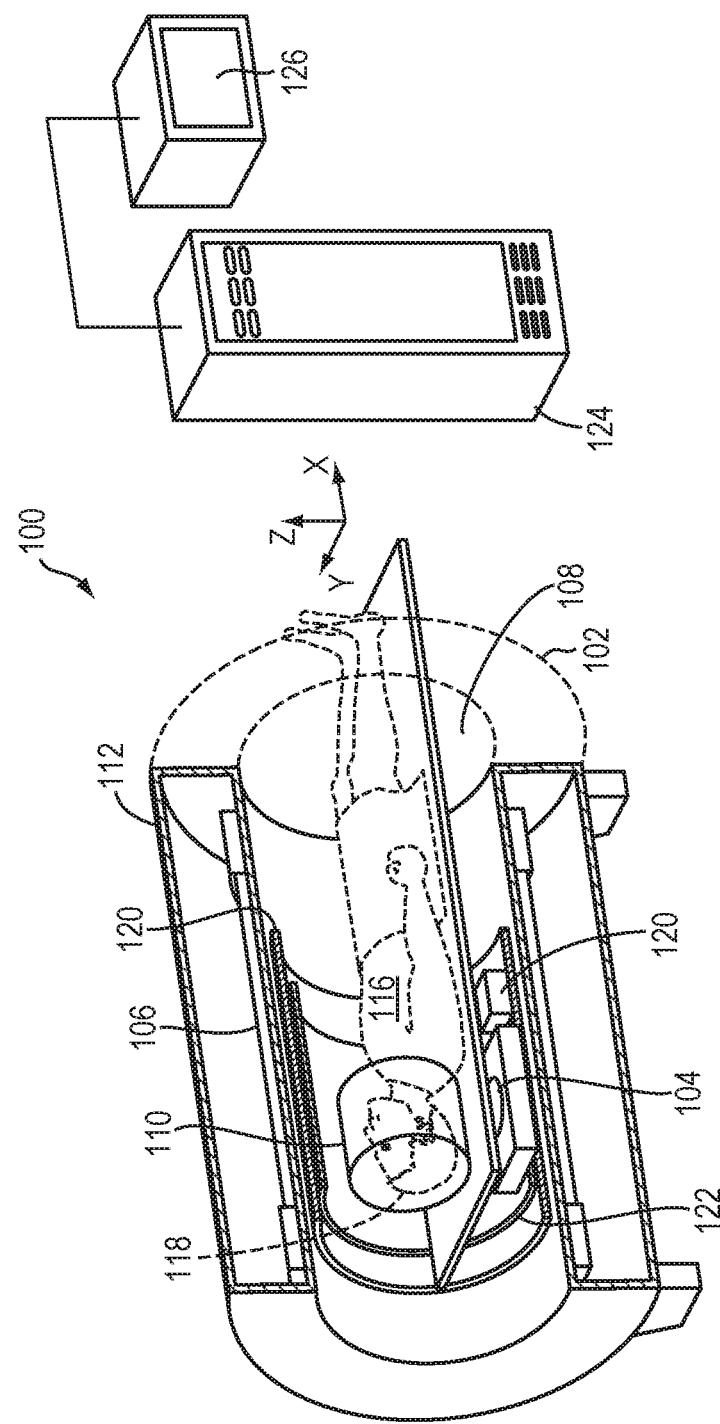
FIG. 1 illustrates an exemplary MRI apparatus in accordance with various embodiments of the present invention.

FIG. 1 shows an exemplary MRI system in or for which the techniques for performing MR thermometry and detecting measurement artifacts in MR thermometry in accordance with various embodiments of the present invention may be implemented. The illustrated MRI system 100 comprises an MRI machine 102. If an MR-guided procedure is being performed, a medical device (e.g., an ultrasound transducer) 104 may be disposed within the bore of the MRI machine 102. Since the components and operation of the MRI machine are well-known in the art, only some basic components helpful in the understanding of the system 100 and its operation will be described herein.

The MRI machine 102 typically comprises a cylindrical electromagnet 106, which generates a static magnetic field within a bore 108 of the electromagnet 106. The electromagnet 106 generates a substantially homogeneous magnetic field within an imaging region 110 inside the magnet bore 108. The electromagnet 106 may be enclosed in a magnet housing 112. A support table 114, upon which a patient 116 lies, is disposed within the magnet bore 108. A region of interest 118 within the patient 116 may be identified and positioned within the imaging region 110 of the MRI machine 102.

A set of cylindrical magnetic field gradient coils 120 may also be provided within the magnet bore 108. The gradient coils 120 also surround the patient 116. The gradient coils 120 can generate magnetic field gradients of predetermined magnitudes, at predetermined times, and in three mutually orthogonal directions within the magnet bore 108. With the field gradients, different spatial locations can be associated with different precession frequencies, thereby giving an MR image its spatial resolution. An RF transmitter coil 122 surrounds the imaging region 110 and the region of interest 118. The RF transmitter coil 122 emits RF energy in the form of a magnetic field into the imaging region 110, including into the region of interest 118.

The RF transmitter coil 122 can also receive MR response signals emitted from the region of interest 118. The MR response signals are amplified, conditioned and digitized into raw k-space data using a controller 124, as is known by those of ordinary skill in the art. The controller 124 further processes the raw k-space data using known computational methods, including fast Fourier transform (FFT), into an array of image data. The image data may then be displayed on a monitor 126, such as a computer CRT, LCD display or other suitable display.

In typical MR imaging procedures, the emission of the RF excitation pulse, the application of the field gradients in various directions, and the acquisition of the RF response signal take place in a predetermined sequence. For example, in some imaging sequences, a linear field gradient parallel to the static magnetic field is applied simultaneously with the excitation pulse to select a slice within the three-dimensional tissue for imaging. Subsequently, time-dependent gradients parallel to the imaging plane may be used to impart a position-dependent phase and frequency on the magnetization vector. Alternatively, an imaging sequence may be designed for a three-dimensional imaging region. Time sequences suitable for PRF thermometry include, for example, gradient-recalled echo (GRE) and spin echo sequences.

The time-varying RF response signal, which is integrated over the entire (two- or three-dimensional) imaging region, is sampled to produce a time series of response signals that constitute the raw image data. Each data point in this time series can be interpreted as the value of the Fourier transform of the position-dependent local magnetization at a particular point in k space, where k is a function of the time development of the gradient fields. Thus, by acquiring a time series of the response signal and Fourier-transforming it, a real-space image of the tissue (i.e., an image showing the measured magnetization-affecting tissue properties as a function of spatial coordinates) can be reconstructed from the raw data. Computational methods for constructing real-space image data from the raw data (including, e.g., fast Fourier transform) are generally known to those of skill in the art, and can readily be implemented without undue experimentation in the controller 124 in hardware, software, or a combination of both.

In the presence of ultrasound-induced temperature changes, because the resonance frequency of water protons decreases with increasing temperature, a hot spot may appear in the phase of the image data. Accordingly, for the purpose of PRF thermometry, the controller 124 further includes functionality for extracting phase information from the real-space image data, and computing a real-space map of the temperature-induced phase shift based on images acquired before as well as after (or during) heating of the target tissue (i.e., the baseline and treatment images). From the phase shift map, a map of temperature changes (in units of $\Delta°$ C.) may be computed via multiplication with a constant c that is given by:

$$c = \frac{1}{\gamma \alpha TEB_0}$$

where $\alpha$ is the applicable PRF change coefficient (which is −0.01 ppm/° C. for aqueous tissue), $\gamma$ is the proton gyromagnetic ratio, $B_o$ is the main magnetic field strength, and TE is the echo time of the GRE or other imaging sequence.

The medical device 104 may also be placed in or near the imaging region 110 of the MRI machine 102. In the example shown in FIG. 1, the medical device 104 may be an ultrasonic instrument used for ablating tissue such as fibroids or cancerous (or non-cancerous) tissue, for breaking up occlusions within vessels, for opening the blood-brain barrier or for performing other treatment of tissues on or within the patient 116. In fact, the medical device 104 can be any type of medical instrument, such as a needle, catheter, guidewire, radiation transmitter, endoscope, laparoscope, or other instrument. In addition, the medical device 104 can be configured either for placement outside the patient 116 or for insertion into the patient's body.

During MR thermal imaging (or any medical procedure involving MR temperature mapping) of the region 110, the region of interest 118, which is typically a part of a patient's body, may change its shape and/or position due to movements of the patient's body. For example, in FIG. 1, the region of interest 118 is the patient's head, which may turn slightly either to the left or to the right during the thermal imaging process. If the region of interest 118 is part of the patient's abdominal area, its shape may contract or expand with the patient's respiratory cycle. The changes in shape and/or position of the region of interest 118 may perturb the magnetic field, thereby altering the phases associated with the MR imaging data; as a result, the thermal maps generated therefrom may be inaccurate.

Similarly, during a medical procedure involving MR temperature mapping of the region 110, the medical device 104 may be re-positioned and/or re-oriented one or more times in accordance with a dynamic protocol. Movement of the medical device 104 resulting from the re-positioning and/or re-orientation may change the magnetic field and thereby the phases of the MR imaging data, which in turn results in inaccurate thermal maps.

The present invention provides various approaches to detecting an inaccurate MR thermal map resulting from non-temperature-related factors (such as movement of the patient or nearby objects) during a medical procedure (e.g., ultrasound treatment). These approaches, generally, involve monitoring the temperature at the region of interest 118 using MR thermometry prior to and during the medical procedure, and computationally predicting a temperature increase resulting from the procedure. If the measured temperature increase (for individual pixels or in a region having aggregated pixels) exceeds the computationally predicted temperature increase by more than a predetermined threshold amount, the temperature map corresponding to such pixels or in such a region in the thermal map acquired at the later time may be inaccurate—i.e., the temperature increase for such pixels or in such a region is due to some extraneous artifacts rather than the true tissue response to the medical procedure.

Figure 2A:
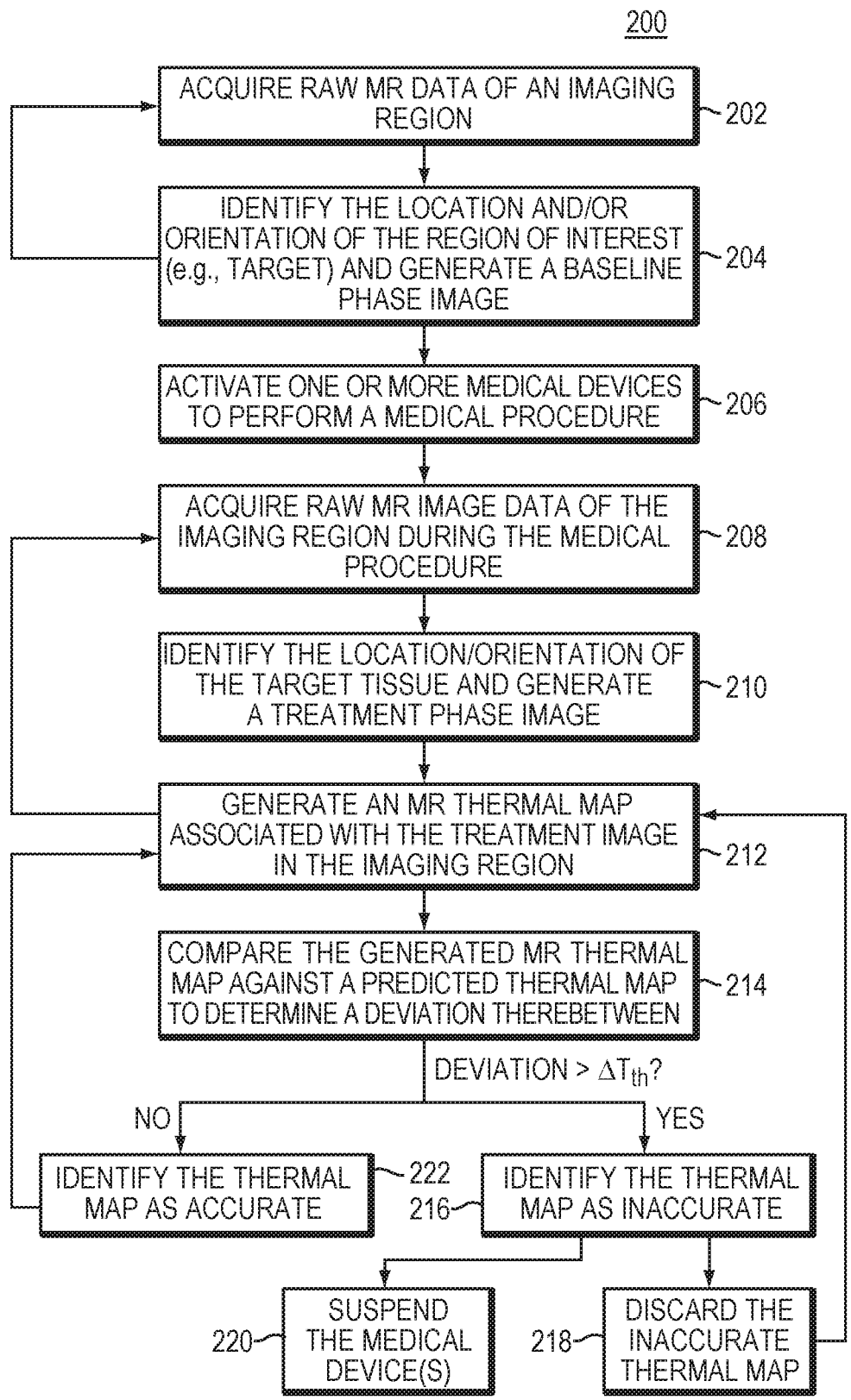
FIGS. 2A and 2B are flow charts illustrating exemplary approaches for detecting an inaccurate MR thermal map in which a temperature increase results from a non-temperature-related factor in accordance with various embodiments of the present invention.

FIG. 2A is a flow chart illustrating an exemplary approach 200 for detecting an inaccurate MR thermal map in which a temperature increase results (at least partially) from a non-temperature-related factor during the medical procedure in accordance with various embodiments. In a first step 202, prior to the medical procedure (e.g., thermal treatment), an MR imaging sequence is carried out to acquire a response signal from the imaging region 110, which is subsequently converted to raw image data (i.e., "k-space data"). In a second step 204, the raw image data is converted (using a fast Fourier transform) to a real-space MR image of the imaging region; a PRF baseline phase image associated with the real-space image can then be generated, and the target tissue (which corresponds to the ROI 118) in the real-space image may be selected. In some embodiments, this selection is manual, i.e., based on user input (e.g., a line drawn with a mouse to circumscribe the target in the image), whereas in other embodiments, the selection is accomplished automatically by a computer algorithm (e.g., a conventional algorithm that thresholds the pixel values, exploiting contrast in the MR image between the target and the surrounding tissues). Steps 202, 204 may be optionally repeated multiple times, e.g., at different stages during a periodic cycle of motion (such as a cardiac or respiratory cycle) for creating a reference library having a series of baseline reference images.

In a third step 206, one or more medical devices associated with the procedure (e.g., the ultrasound transducer 104 for thermal treatment) may be activated to treat the target tissue. During treatment, raw image data of the target region are acquired using the MRI apparatus 100 as described above (step 208). Again, the raw treatment images may be converted to a real-space image and processed to identify the location of the target tissue and generate a PRF treatment phase image (step 210). In a step 212, the PRF treatment phase image is compared against the PRF baseline phase image acquired prior to the thermal treatment, on a pixel-by-pixel basis, to compute the phase differences therebetween; based on the computed phase differences, an MR thermal map associated with the treatment image in the imaging region can be created. Optionally, steps 208-212 may be repeated for monitoring in vivo temperatures of the target and/or non-target tissues during the medical procedure. This is particularly useful in MR-guided thermal therapy (e. g., MRgFUS treatment), where the temperatures of the target and/or non-target tissues are continuously monitored in order to assess the progress of thermal treatment and correct for local differences in heat conduction and energy absorption.

If a reference library of baseline images covering the anticipated range of motion is obtained as described above, a reference baseline image in the library that best matches the acquired treatment image may be selected based on similarity therebetween. The selected baseline and treatment images are then processed to generate the thermal map illustrating the change in temperature in the target/non-target regions. This approach is often referred to as multi-baseline thermometry; exemplary approaches for performing multi-baseline thermometry are described in U.S. Pat. No. 9,814, 909, the entire disclosure of which is hereby incorporated by reference.

To determine whether the acquired thermal map is inaccurate, in various embodiments, the thermal map generated from the MRI measurement in step 212 may be compared against a thermal map predicted using a physical model as further described below (step 214). If the deviation between the measured and predicted thermal maps exceeds a predetermined threshold amount $\Delta T_{th}$ (for individual pixels or in a region over which pixel values are aggregated), the thermal map is deemed inaccurate (step 216). The inaccurate thermal map may then be discarded and new MR imaging data may be acquired to generate a new thermal map (step 218). Additionally or alternatively, the medical device 104 may be suspended until an accurate thermal map is generated so as to avoid damage to the non-target tissue (step 220). In contrast, if the deviation between the measured and predicted thermal maps is equal to or below the predetermined threshold, the thermal map acquired in step 212 is deemed accurate (step 222).

Figure 3A:
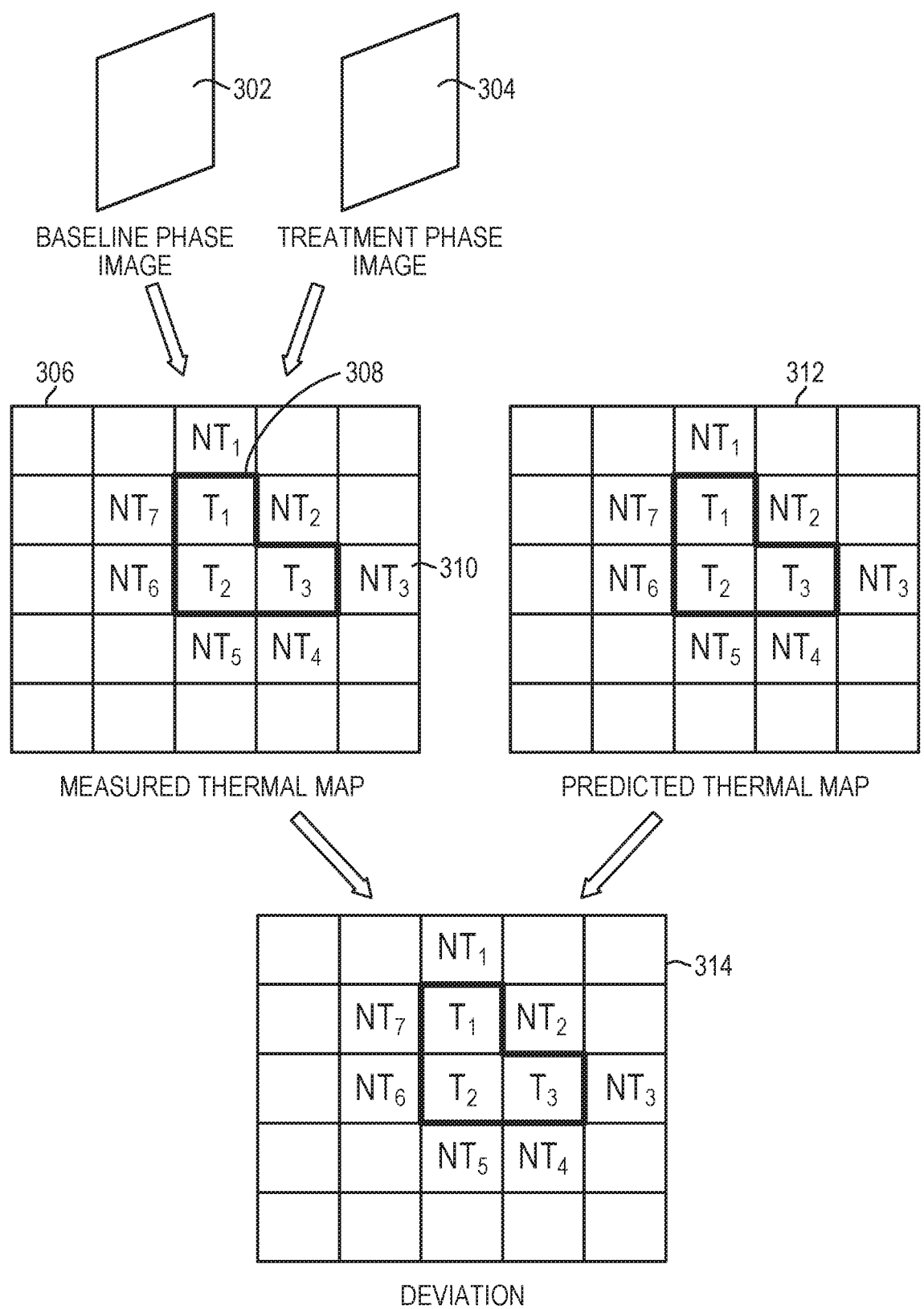
FIGS. 3A-3D depict exemplary temperature-deviation maps illustrating a temperature difference between a measured thermal map and a predicted thermal map at a target region and/or a non-target region in accordance with various embodiments of the present invention.
Figure 3B:
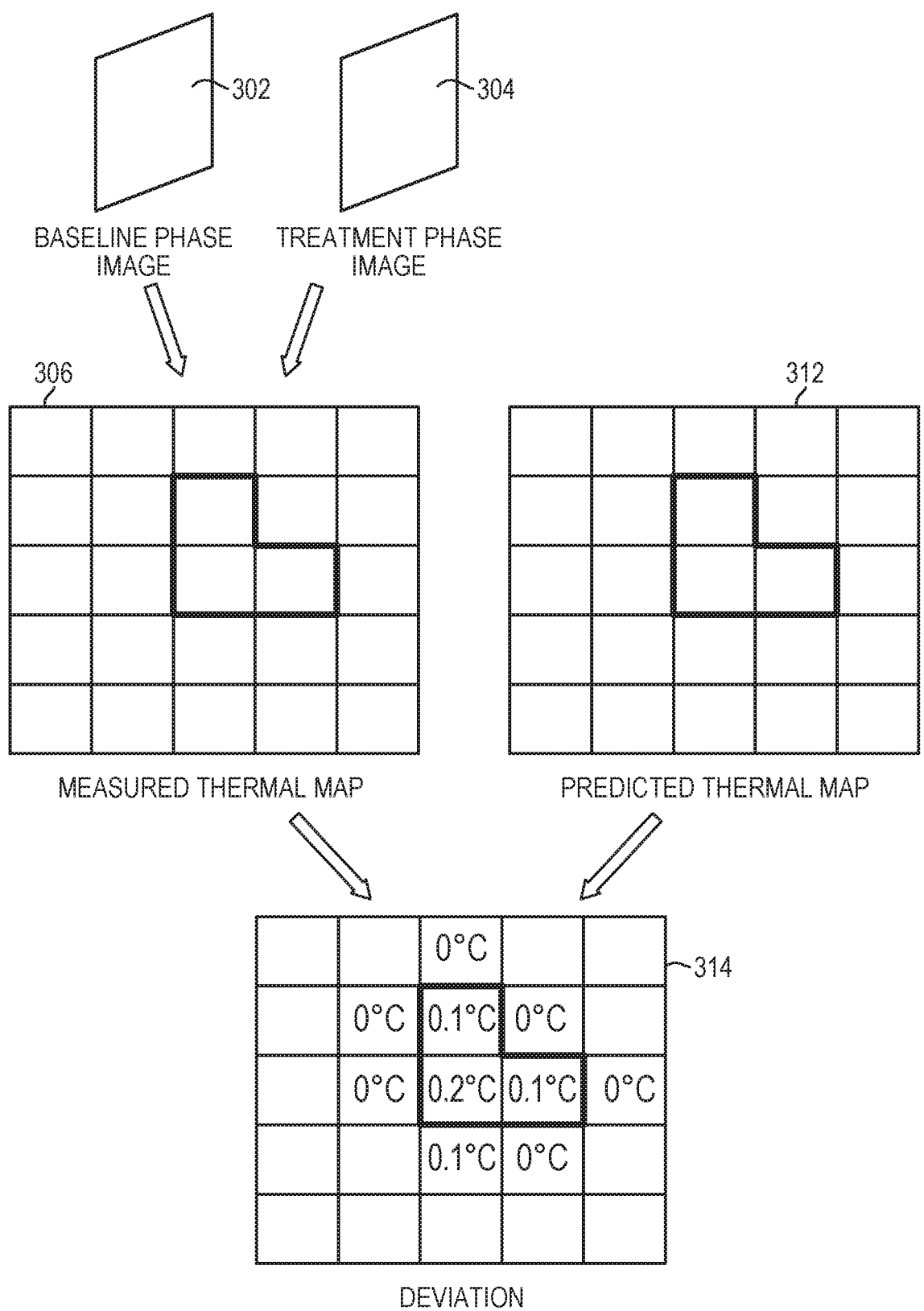

For example, referring to FIG. 3A, the controller 124 may compare the phase differences between the phase images corresponding to the baseline image 302 and the treatment image 304, and based thereon converting the phase differences into temperature differences in a thermal map 306. In addition, the target region 308 includes target pixels $T_1$-$T_3$ and the non-target region 310 surrounding the target region includes non-target pixels $NT_1$-$NT_7$ in the map 306. In some embodiments, the controller further creates a thermal map 312 indicating a predicted temperature increase resulting from the thermal treatment as further described below. The difference between the measured and predicted thermal maps 306, 312 may then be determined on a pixel-by-pixel basis (as shown in a deviation map 314) and compared against the predetermined thresholds. For example, the predetermined thresholds for the differences corresponding to the individual pixels in the target region $T_1$-$T_3$ and non-target region $NT_1$-$NT_7$ are 0.5° C. and 0.1° C., respectively, and the thresholds for the deviations in the target and non-target regions having aggregated pixels are 1.2° C. and 0.5° C., respectively. With reference to FIG. 3B, because the deviation between the measured and predicted temperatures for each of the target pixels $T_1$-$T_3$ and non-target pixels $NT_1$-$NT_7$ is smaller than the predetermined threshold, and the aggregated temperature deviations for the target pixels and non-target pixels are 0.4° C. and 0.1° C., respectively (both smaller than the predetermined thresholds), the measured thermal map 306 is deemed accurate.

Figure 3C:
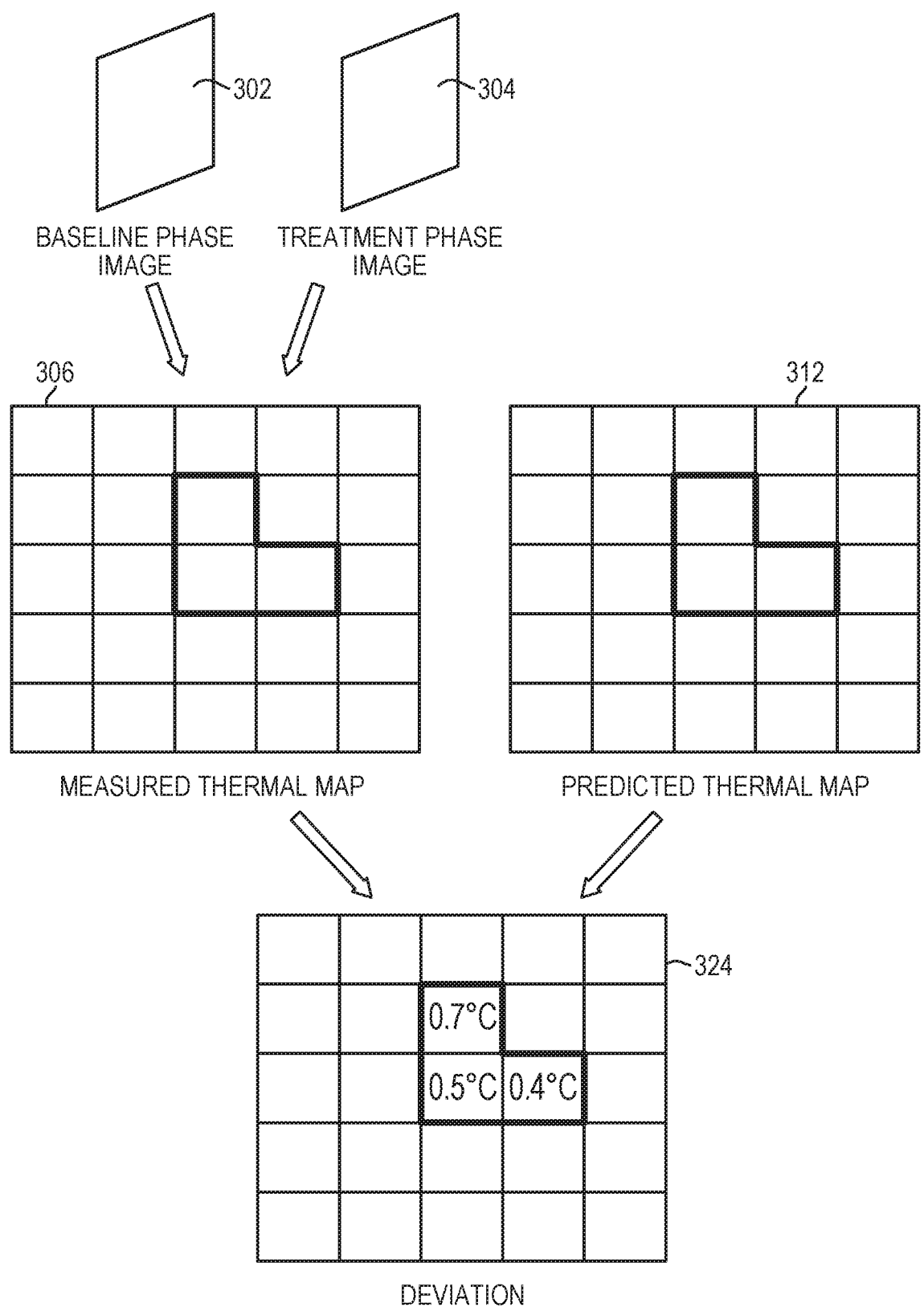
Figure 3D:
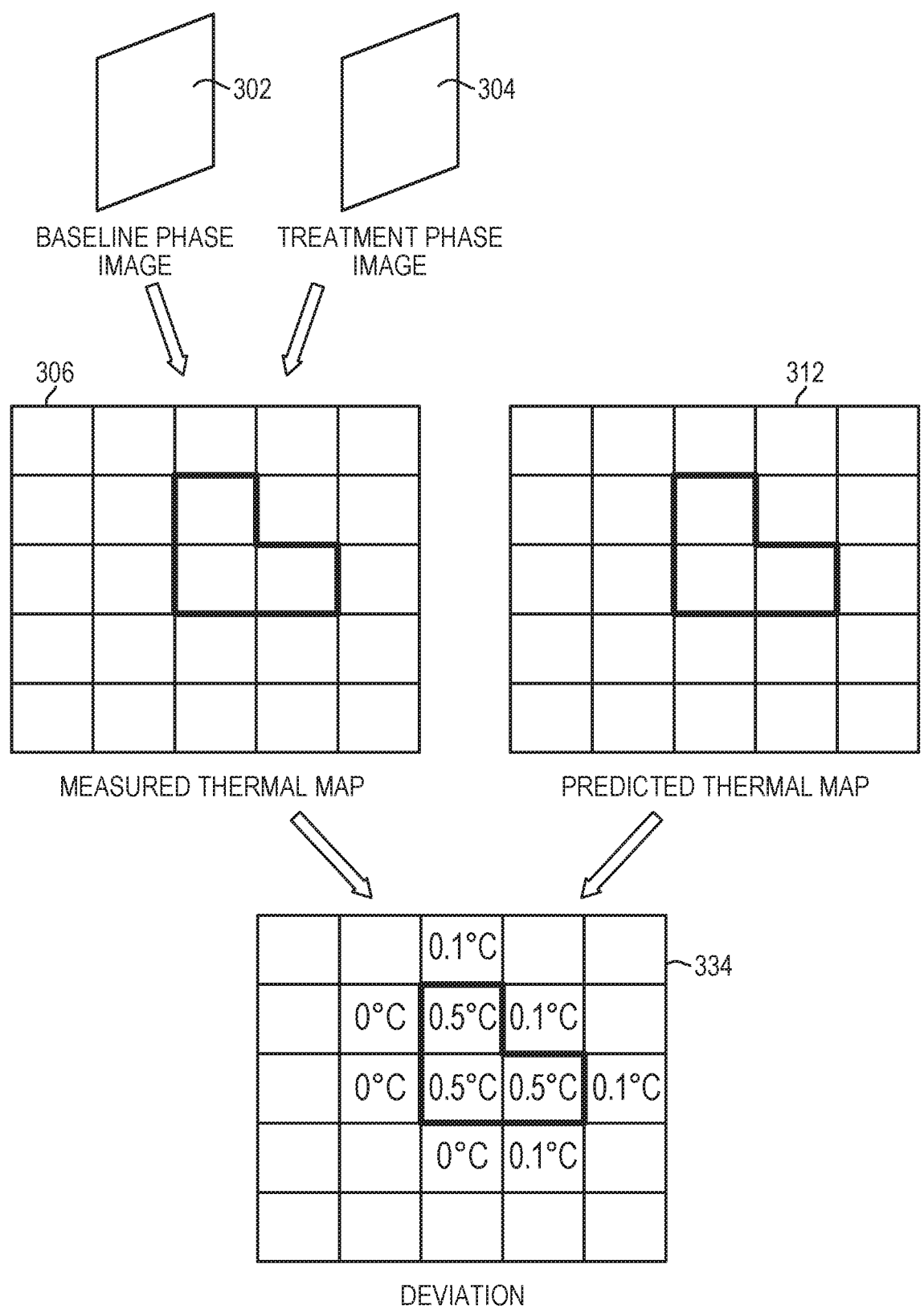

In contrast, when the deviation between the measured and predicted thermal maps for individual pixels and/or aggregated pixels in the target and/or non-target regions exceeds the predetermined thresholds, the thermal map 306 is determined inaccurate. For example, referring to FIG. 3C, because the temperature deviation in map 324 at the target pixel $T_1$ exceeds the predetermined threshold (0.5° C.), the thermal map 306 is considered inaccurate. Similarly, referring to FIG. 3D, the deviation between the measured and predicted thermal maps is depicted in map 334. Although the deviation for each of the target pixels $T_1$-$T_3$ and non-target pixels $NT_1$-$NT_7$ does not exceed the predetermined threshold (0.5° C. and 0.1° C., respectively), the aggregated temperature difference in the target pixels is 1.5° C. exceeding the predetermined aggregated threshold 1.2° C.; as a result, the thermal map 306 is considered inaccurate.

After the thermal map 306 is generated, the processing time for determining the change in temperature, comparing the measured temperature change against the predicted value to determine a deviation therebetween, and determining whether the deviation exceeds the predetermined threshold is relatively fast (compared with acquisition of the MR imaging data). Accordingly, the approaches described above may advantageously determine accuracy of the newly acquired thermal map in real-time (or substantially in real-time) during the medical procedure.

Figure 2B:
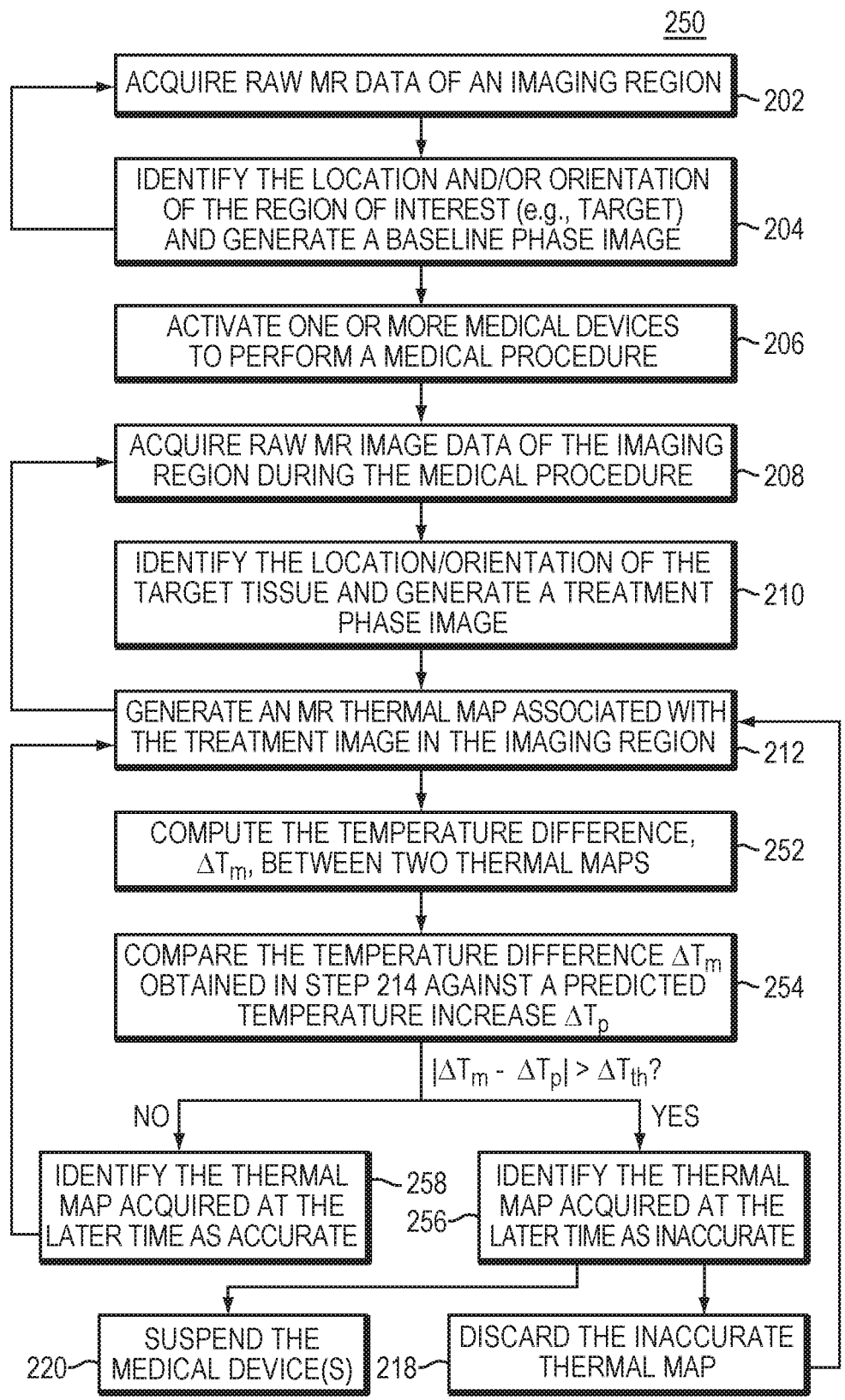

FIG. 2B is a flow chart illustrating another method 250 for detecting an inaccurate MR thermal map resulting from a one or more factors unrelated to tempeartuer during the medical procedure in accordance with various embodiments. Similar to the method 200 shown in FIG. 2A, steps 202-212 are performed in the method 250. But in this method, two thermal maps acquired at different times during the medical procedure are analyzed on a pixel-by-pixel basis to determine the temperature difference, $\Delta T_m$, between them (step 252); the computed difference is then compared against a predicted temperature increase, $\Delta T_p$ (step 254). If the computed temperature difference $\Delta T_m$ exceeds the predicted temperature increase $\Delta T_p$ by more than a predetermined threshold amount, $\Delta T_{th}$ (for individual pixels or in a region having aggregated pixels), the thermal map acquired at the later time may be identified as inaccurate, indicating that the temperature increase corresponding to such pixels or in such a region is due to some extraneous artifacts rather than the true tissue response to the medical procedure (step 256). If the computed temperature difference between the two thermal maps does not deviate significantly from the predicted temperature increase (i.e., it is below the predetermined threshold amount for the aggregated or individual pixels, $|\Delta T_m - \Delta T_p| \leq \Delta T_{th}$), the thermal map acquired at the later time is deemed accurate (step 258).

Figure 4:
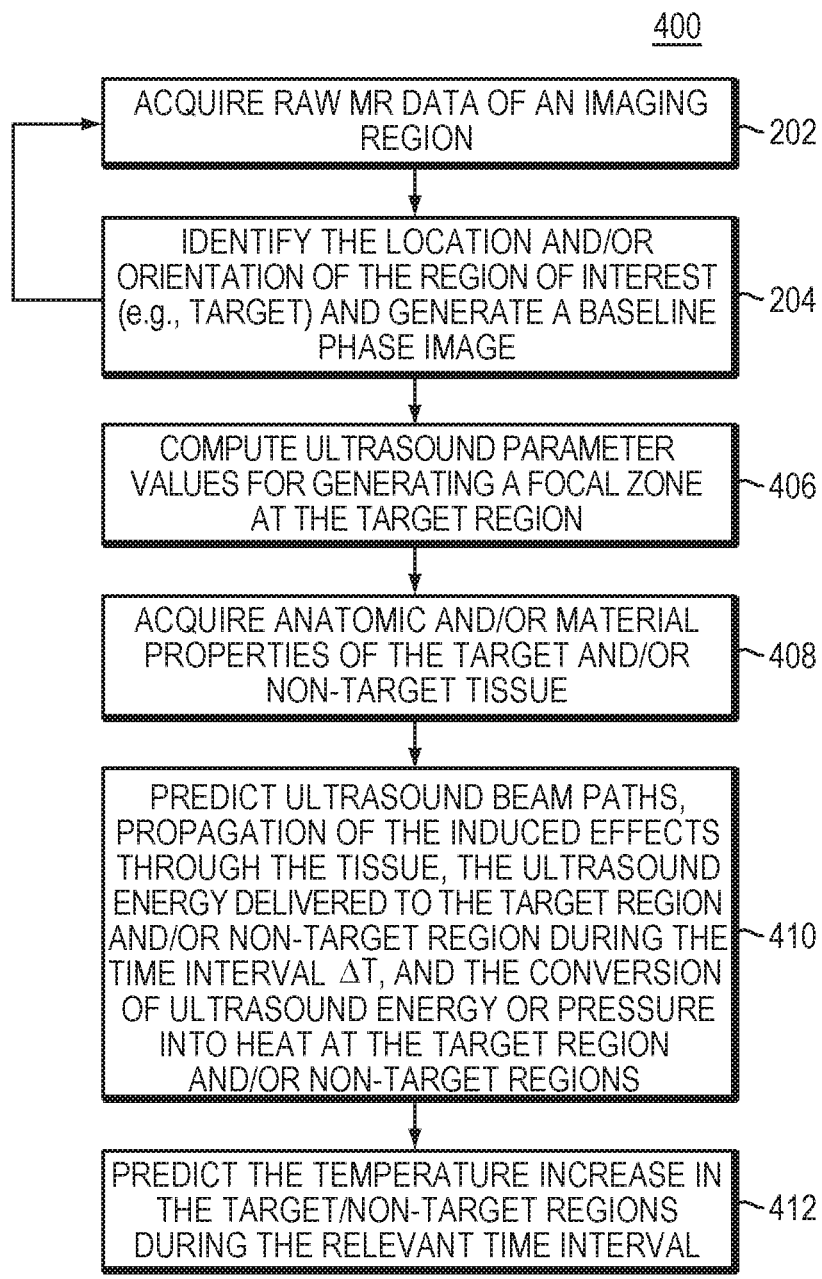
FIG. 4 is a flow chart illustrating an exemplary approach for predicting a change in temperature in the target/non-target regions during a medical procedure in accordance with various embodiments of the present invention.

In various embodiments, the temperature increase at a given time $t=t_1$ during the medical procedure or between two thermal maps acquired at times $t=t_1$ and $t=t_2$ is predicted based on tissue characteristics of the target and/or non-target regions and the energy (e.g., acoustic energy in ultrasound treatment) deposited in the target and/or non-target regions during the relevant time interval $\Delta t$ (e.g., from the time commencing the thermal treatment to acquisition of the thermal map or from $t=t_1$ to $t=t_2$). FIG. 4 depicts an exemplary approach for predicting the temperature increase resulting from the thermal treatment in accordance with various embodiments. In a typical ultrasound treatment, upon determining the location and/or orientation of the target region using approaches described above (e.g., step 204 in FIG. 2A), ultrasound parameter values (e.g., amplitudes, frequencies, phases and/or directions associated with the transducer elements, or time intervals between consecutive series of sonications) may be computed so that a focal zone is created at the target region (in step 406). This step generally involves applying a physical model and taking into account the geometry as well as the position and orientation of the ultrasound transducer relative to the target region. In addition, tissue characteristics, such as anatomic characteristics (e.g., the type, property, structure, thickness, density, etc.) and/or material characteristics (e.g., the speed of sound) of the intervening tissue located on the beam path between the transducer and the target region may be included in the physical model in order to predict and correct for beam aberrations resulting therefrom. In one implementation, the anatomic characteristics of the intervening tissue are acquired using an imaging device, such as the MRI apparatus 100 (as depicted in FIG. 1), a CT device, a PET device, a SPECT device, or an ultrasonography device. For example, based on the acquired images, a tissue model characterizing the material characteristics of the intervening tissue may be established. The tissue model generally includes multiple tissue types or layers (e.g., for ultrasound focusing into the skull, layers of cortical bone, bone marrow, and soft brain tissue) and characterizes their respective anatomic and/or material properties. The tissue model may take the form of a 3D table of cells corresponding to the voxels representing the target and/or non-target tissue; the cells have attributes whose values represent characteristics of the tissue, such as the speed of sound, that are relevant to aberrations that occur when the beam traverses the tissue. The voxels are obtained tomographically by the imaging device and the type of tissue that each voxel represents can be determined automatically by conventional tissue-analysis software. Using the determined tissue types and a lookup table of tissue parameters (e.g., speed of sound by type of tissue), the cells of the tissue model may be populated. Further detail regarding creation of a tissue model that identifies the speed of sound, heat sensitivity and/or thermal energy tolerance of various tissues may be found in U.S. Patent Publication No. 2012/0029396, the entire disclosure of which is hereby incorporated by reference.

The acoustic power of the beam in the focal zone is (at least partially) absorbed by the target tissue, thereby generating heat and raising the temperature of the tissue to a point where the cells are denatured and/or ablated. The degree of ultrasound absorption over a propagation length in tissue is a function of frequency, given by:

$$P_t = P_0 \times (1 - 10^{-2\alpha fz}) 10^{-2\alpha f},$$

where $P_0$ represents the initial acoustic power of ultrasound beams emitted from the transducer; f represents the transmitting frequency of the ultrasound (measured in MHz); a represents the absorption coefficient at the relevant frequency range (measured in $cm^{-1} \cdot MHz^{-1}$) and may be obtained from known literature; z represents the focal length—i.e., the distance, measured in cm, that the ultrasound beam propagates through the tissue prior to reaching the target; and $P_t$ represents the acoustic power at the target region. Accordingly, in various embodiments, the controller 124 processes the acquired images to further characterize the anatomic and/or material properties of the target and/or non-target tissue and include them in the tissue model (in step 408). For example, the 3D table of cells in the tissue model may further include attributes whose values represent the absorption coefficient associated with the target/non-target tissue.

Thus, based on the anatomic and/or material properties of the target/non-target tissue characterized by the tissue model and the employed ultrasound parameter values, the physical model may predict ultrasound beam paths, the propagation of the induced effects through the tissue, the ultrasound energy delivered to the target region and/or non-target region during the time interval $\Delta t$, and the conversion of ultrasound energy or pressure into heat at the target region and/or non-target regions (in step 410). In some embodiments, the computational physical model further takes the form of (or include) differential equations (such as the Pennes model and a bioheat equation) to simulate heat transfer in tissue, thereby predicting the temperature increase in the target/non-target regions during the time interval $\Delta t$ (in step 412).

Generally, the Pennes model is based on the assumption that the rate of heat transfer between blood and tissue, $h_b$, is proportional to the product of the blood perfusion rate $W_b$ (measured in $kg/(s \ m^3)$) and the difference between the arterial blood temperature $T_a$ and the local tissue temperature $T(x,y,z)$: $h_b = W_b C_b (T_a - T)$, where $C_b$ is the specific heat of blood (measured in $J/(K \ kg)$). Adding a heat-transfer contribution due to thermal conduction in the tissue, and taking into account metabolic heat generation at a rate $Q_m$ (measured in $J/(s \ m^3)$), the Pennes equation expresses the thermal energy balance for perfused tissue in the following form:

$$\rho C \frac{\partial T}{\partial t} = k \left( \frac{\partial^2 T}{\partial x^2} + \frac{\partial^2 T}{\partial y^2} + \frac{\partial^2 T}{\partial z^2} \right) + W_b C_b (T_a - T) + Q_m + Q_{ext}.$$

where $\rho$, C, and k are the density, heat capacity, and thermal conductivity (measured in $J/(s \ m \ K)$) of the tissue, respectively, and $Q_{ext}$ represents the thermal power extracted per unit volume of tissue from the thermal treatment. Thus, by solving the Pennes equation numerically using any of a variety of methods known to persons of skill in the art (such as finite-difference and finite-element methods), a temperature map at a given point in time can be computed. Accordingly, the thermal map indicating the change in temperature after application of the thermal treatment at a given time or between two times $t=t_1$ and $t=t_2$ can be determined. Approaches to computationally predicting a temperature increase during ultrasound treatment are provided, for example, in U.S. Patent Publication Nos. 2012/0071746 and 2015/0359603, the entire disclosures of which are hereby incorporated by reference.

Figure 5A:
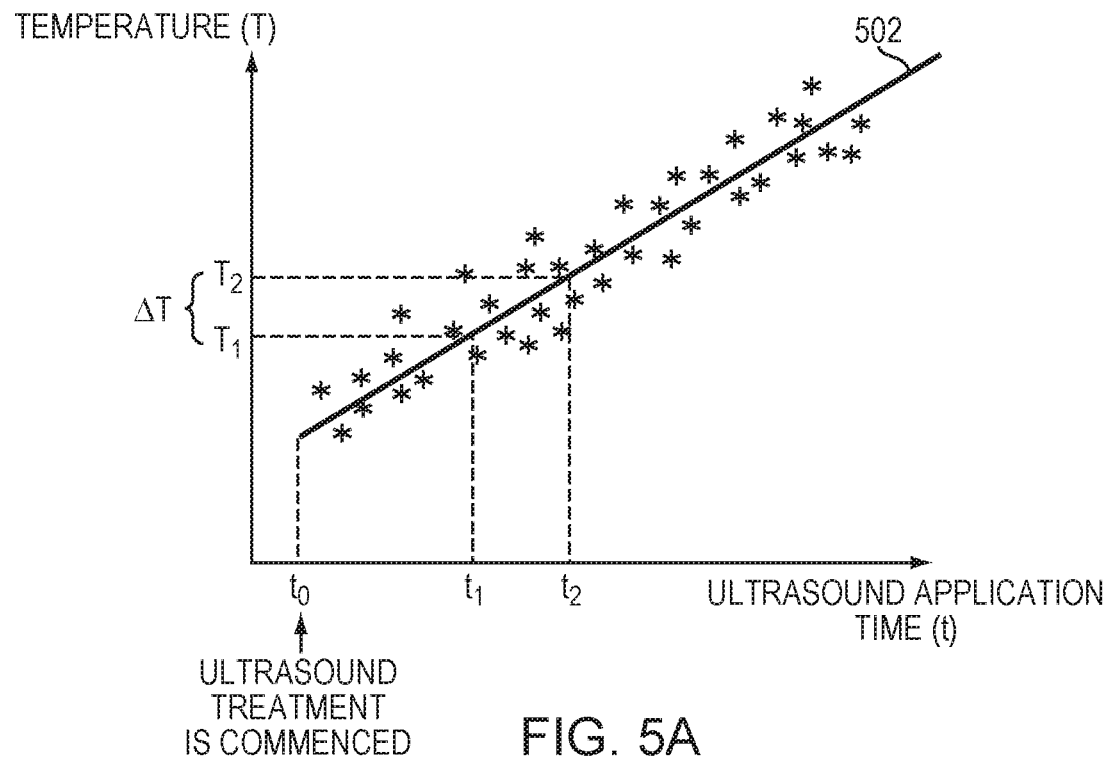
FIG. 5A depicts the relationship between a temperature change at the target region and an application time of the acoustic energy in accordance with various embodiments of the present invention.
Figure 5B:
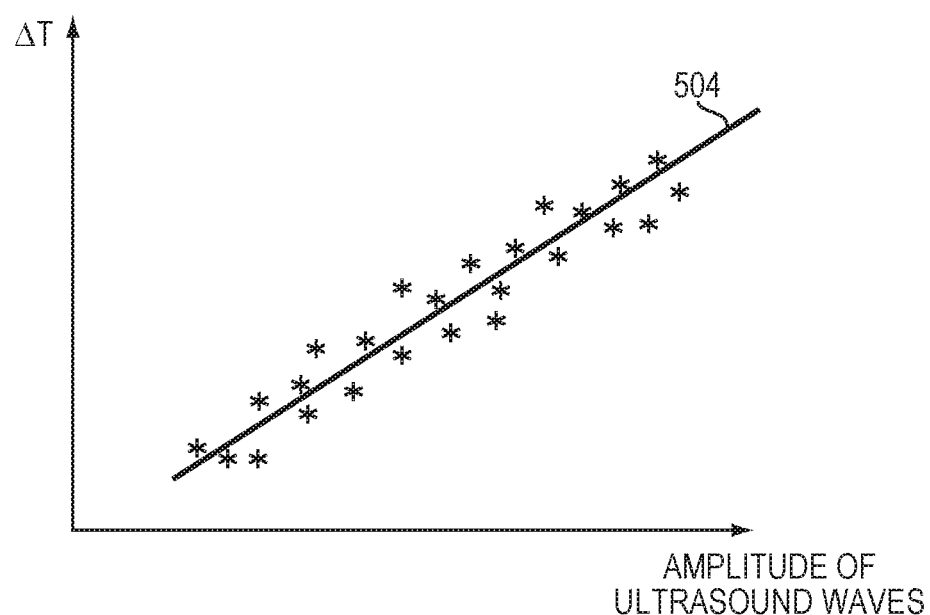
FIG. 5B depicts the relationship between a temperature change at the target region and an amplitude of the applied ultrasound waves in accordance with various embodiments of the present invention.

Alternatively or additionally, the temperature change resulting from the thermal treatment may be predicted using a statistical model. For example, the statistical model may include historical data of the accumulated acoustic energy or temperature increase during the treatment interval, $\Delta t$, performed on the same or different patient previously. In one embodiment, MR images acquired in previous thermal treatment on the same type of target tissue and/or non-target tissue are retrospectively studied to determine the heat absorbed in the target/non-target tissues. In addition, the ultrasound parameter values employed for the previous treatment are analyzed to determine the acoustic power transmitted to the target/non-target tissues. Based on these retrospective studies, a statistical model relating the transmitted acoustic power to the accumulated acoustic energy or temperature increase at the target/non-target regions may be straightforwardly established. Ultrasound parameter values employed in the current treatment may then be applied to the statistical model to predict the accumulated acoustic energy or temperature increase during the treatment interval, $\Delta t$. For example, referring to FIG. 5A, the retrospective study may illustrate that the increase in temperature at the target region having type A tissue positively correlates to the application time of the acoustic energy. The statistical model may thus include a regression 502 performed on the measured temperatures against the durations of ultrasound application time; the regression 502 may then be applied to predict the temperatures of the type-A target tissue at ultrasound application times $t=t_1$ and $t=t_2$. Subsequently, a temperature increase $\Delta T$ in the target tissue from $t=t_0$ (i.e., when the ultrasound treatment is commenced) to $t=t_1$ (or from $t=t_1$ to $t=t_2$) can be computed. Similarly, referring to FIG. 5B, the retrospective study may indicate that the temperature increase $\Delta T$ at the target region within the time interval $\Delta t$ positively correlates to the amplitude of the ultrasound waves. By performing a regression 504 on the measured temperature increases against the ultrasound amplitudes, the temperature increase at the target tissue can be computed based on the amplitude of the currently applied sonications.

It should be noted that the approaches described herein for predicting the accumulated energy and/or temperature increase at the target/non-target regions are exemplary only; any suitable approaches for predicting the accumulated energy and/or temperature increase during thermal treatment may be used in the methods 200, 250 to detect inaccurate MR thermal maps as described above, and are thus within the scope of the present invention.

In addition, the predetermined threshold(s) for deciding whether the temperature increase in a thermal map results from a tissue response to the thermal treatment or some extraneous artifacts (described in steps 216, 222, 256, 258) may be fixed or dynamically varied. Generally, the threshold (s) may represent a significant clinical effect on the target/non-target tissue resulting from the medical procedure. As used herein, "significant clinical effect" means having an undesired (and sometimes the lack of a desired) effect on tissue that is considered significant by clinicians, e.g., the onset of damage thereto or other clinically adverse effect, whether temporary or permanent. In some embodiments, the thresholds are determined based on the types, material properties, and/or locations of the target/non-target tissue. For example, because the target tissue is to be ablated in ultrasound treatment, the thresholds of temperature increase corresponding to the target tissue may be larger than those corresponding to the non-target tissue. In addition, if the non-target tissue next to the target region is a sensitive and/or important organ, the risk of damaging the non-target organ is high, and the need for protecting the sensitive/important non-target organ is heightened. Consequently, in this situation, the predetermined thresholds corresponding to the temperature increase in the non-target tissue may be smaller than for the situation where non-sensitive and/or clinically unimportant non-target tissue surrounds the target region. Thus, in one implementation, the thresholds are predetermined by the controller 124 based on, for example, the anatomical properties of the target/non-target tissue acquired using the imaging device and/or the tissue model characterizing the material properties of the target and/or non-target tissue as described above.

In some embodiments, the size of the threshold positively correlates to the amount of acoustic energy transmitted to the target region, so that the threshold is small for relatively small acoustic energies and larger (e.g., 10% or 20% larger) for relatively larger acoustic energies. For example, during thermal treatment, the acoustic energy transmitted to the target may increase from $E_1$ to $E_2$ ($E_2=E_1+\Delta E$); the threshold values associated with individual pixels in the target region may be dynamically increased from $T_1°$ C. to $T_2°$ C. ($T_2=T_1+\Delta T$). As a result, at a higher acoustic energy, a larger discrepancy between the measured and predicted temperatures is required to determine that the measured thermal map is inaccurate.

The threshold value(s) may be adjusted based on other parameters relevant to the temperature measurements. For example, MR response signals having a smaller signal-to-noise ratio (i.e., a higher noise level) received in steps 202, 208 may correspond to a larger threshold value compared with MR response signals having a larger signal-to-noise ratio (i.e., a lower noise level). Thus, if the thermal map has a higher noise level, a larger discrepancy between the measured and predicted temperatures is required to determine that the measured thermal map is flawed. In some embodiments, the threshold value(s) may be dynamically varied based on the difference between the measured and predicted temperatures. For example, each measured thermal map in the target region may have a temperature difference from the predicted thermal map; the threshold can be defined statistically in terms of the mean temperature difference, e.g., ½ or 1 standard deviation from the mean temperature difference of the entire measured thermal maps.

Figure 6:
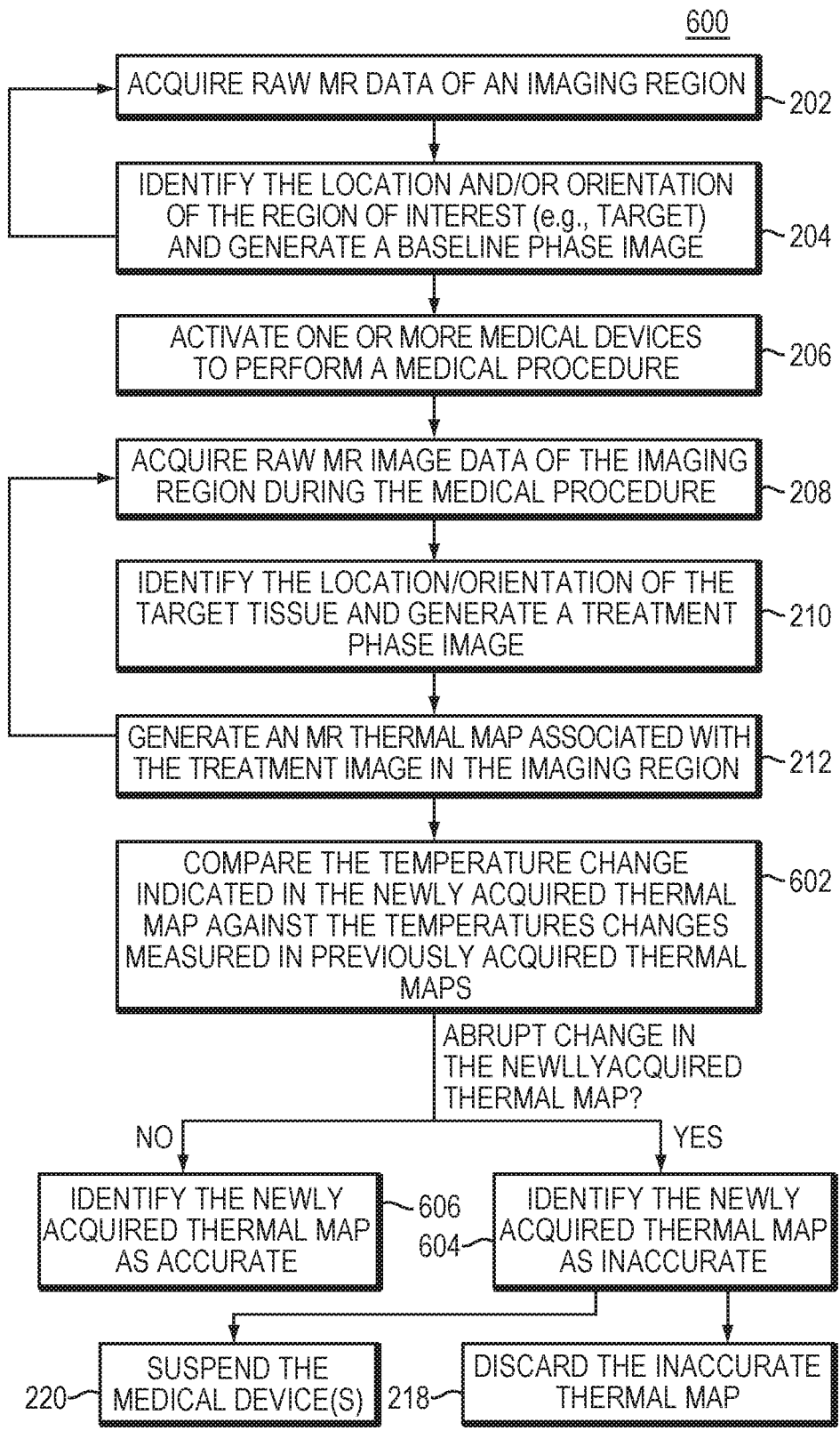
FIG. 6 is a flow chart illustrating another exemplary approach for detecting an inaccurate MR thermal map in which a temperature increase results from a non-temperature-related factor in accordance with various embodiments of the present invention.
Figure 7:
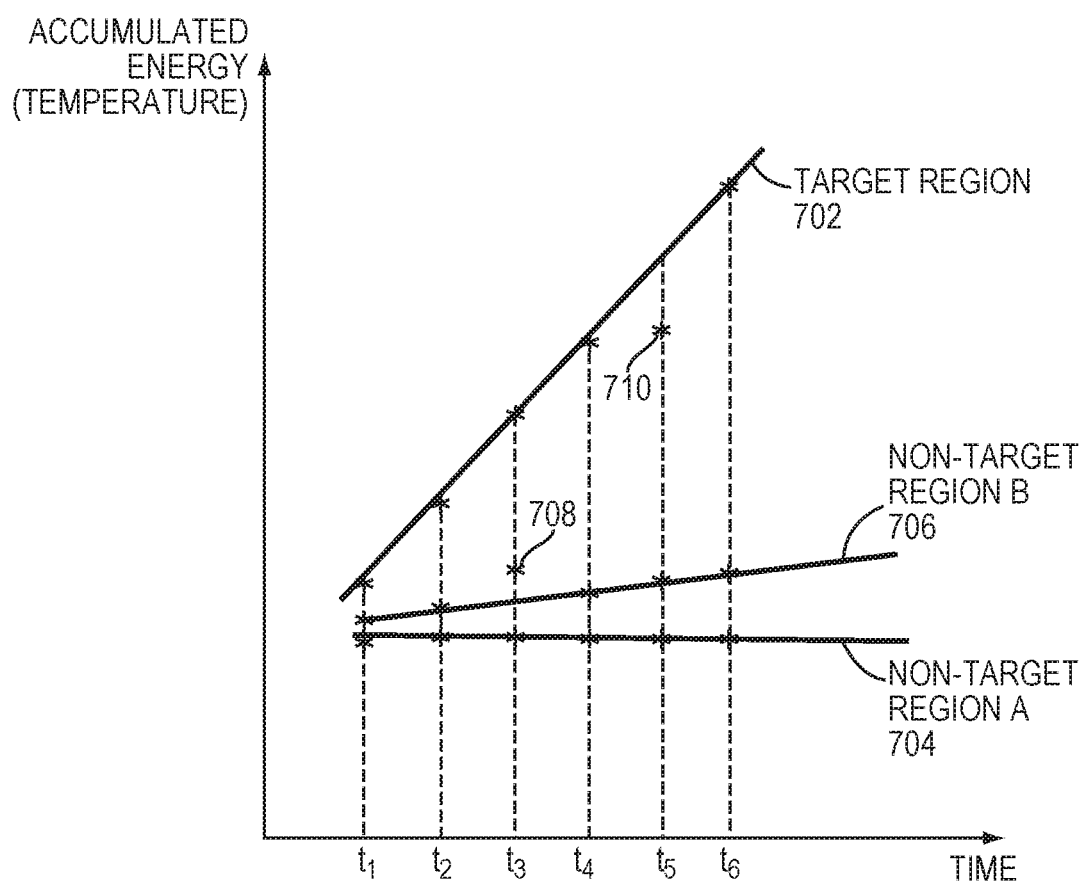
FIG. 7 depicts various relationships between a temperature change at the target and non-target regions and an application time of the acoustic energy in accordance with various embodiments of the present invention.

FIG. 6 is a flow chart illustrating another exemplary approach 600 for detecting an inaccurate MR thermal map in which an increase in temperature during a medical procedure results from non-temperature-related factors in accordance with various embodiments. Similar to the methods 200, 250 in FIGS. 2A and 2B, steps 202-212 are performed in approach 600 to generate a thermal map indicating a change in temperature resulting from the treatment. Approach 600, however, does not require prediction of the temperature increase as required in the methods 200, 250. Rather, detection of the inaccurate map is based on historical imaging data acquired during the medical procedure. For example, referring to FIG. 7, assuming that the transmitted ultrasound power remains constant during treatment, the energy accumulated (and thereby the temperature) at the target region may be expected to increase gradually with time (as shown in line 702); similarly, the temperature at the non-target region may remain constant (e.g., line 704) or increase with time but have an increasing rate slower than that of the temperature increase in the target region (e.g., line 706). Thus, if the target or non-target region in a particular temperature map has an abrupt increase or decrease in temperature (e.g., compared with the average increase or decrease for the same region over the previous few images), this indicates that the temperature map is incorrect at the noted region. For example, at time $t=t_3$, the temperature at a non-target region B shows an abrupt increase 708, this indicates that the thermal map at the non-target region B is flawed. Similarly, the abrupt temperature decrease 710 in the target region at time $t=t_5$ indicates that the thermal map in the target region acquired at time $t=t_5$ is inaccurate. Again, the temperature evolution at the target/non-target tissues during treatment as depicted in FIG. 7 may be monitored based on individual pixels and/or aggregate pixel values associated with the target/non-target regions. Accordingly, referring again to FIG. 6, after multiple thermal maps are acquired during thermal treatment, the controller may compare the temperature change indicated in the newly acquired thermal map against the temperatures changes measured in previously acquired thermal maps (step 602). If the newly acquired thermal map shows an abrupt temperature change, it indicates that the thermal map may be inaccurate (step 604). If no abrupt temperature change is detected, it then indicates that the newly acquired thermal map is accurate (step 606).

Although the invention has been described with reference to utilizing MR thermometry for monitoring the temperature at the target and/or non-target regions during a medical procedure (e.g., ultrasound thermal treatment), it is not intended for this arrangement to limit the scope of the invention. For example, a temperature sensor may be implemented to measure the temperature during treatment. Moreover, it is to be understood that the features of the various embodiments described herein are not necessarily mutually exclusive and can exist in various combinations and permutations, even if such combinations or permutations are not made express herein, without departing from the spirit and scope of the invention. In fact, variations, modifications, and other implementations of what is described herein will occur to those of ordinary skill in the art without departing from the spirit and the scope of the invention.

In general, functionality for performing MR thermometry and detecting an inaccurate thermal map in MR thermometry, including, for example, analyzing imaging data of the target and/or non-target regions acquired using one or more imaging modalities (e.g., MR imaging) prior to and/or during the medical procedure, determining the target location, generating a baseline phase image based on the imaging data, generating an MR thermal map, computing the temperature difference between two thermal maps, establishing a computational physical model and/or a statistical model to predict a temperature increase during treatment, comparing the measured temperature (or temperature change) against the predicted temperature (or temperature increase), determining whether the thermal map acquired at the later time is inaccurate based on the comparison and/or historical imaging data, computing ultrasound parameter values for generating a focal zone at the target region, activating the medical device (e.g., ultrasound transducer) based on the determined parameter values, acquiring anatomic and/or material properties of the target and/or non-target tissue, computationally predicting ultrasound beam paths, computationally predicting propagation of the induced effects through the tissue, computationally predicting the ultrasound energy delivered to the target region and/or non-target region during a time interval, and computationally predicting the conversion of ultrasound energy or pressure into heat at the target region and/or non-target regions, as described above, whether integrated within the controller 124 of the imaging device (e.g., MRI apparatus 100), and/or provided by a separate external controller or other computational entity or entities, may be structured in one or more modules implemented in hardware, software, or a combination of both. The controller 124 may include one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C #, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

In addition, the term "controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for performing magnetic resonance (MR) thermometry, the system comprising:
    a magnetic resonance imaging (MRI) unit; and
    a controller in communication with the MRI unit and configured to:
    (i) cause the MRI unit to acquire at least one baseline MR phase image of an imaging region and at least one treatment MR phase image of the imaging region subsequent to a temperature change of a subregion within the imaging region;
    (ii) electronically generate a thermal map pixelwise indicating the temperature change of the subregion based at least in part on a proton-resonance frequency shift of the acquired baseline MR phase image relative to the treatment MR phase image;
    (iii) computationally predict, without reference to the generated thermal map, the temperature change of the subregion based at least in part on energy deposited in the subregion during treatment; and
    (iv) determine whether the thermal map is inaccurate based at least in part on the temperature change of the subregion indicated by the thermal map and the predicted temperature change of the subregion, and, if so, generate a new thermal map pixelwise indicating the temperature change of the subregion based at least in part on the acquired baseline MR phase image and treatment MR phase image.

2. The system of claim 1, wherein the controller is further configured to:
    compare the temperature change in the generated thermal map against the predicted temperature change so as to determine a deviation therebetween; and
    compare the deviation against a predetermined threshold.

3. The system of claim 2, wherein the controller is further configured to determine that the thermal map is inaccurate upon determining that the deviation exceeds the predetermined threshold.

4. The system of claim 3, wherein the predetermined threshold is a fixed value.

5. The system of claim 3, wherein the controller is further configured to adjust the predetermined threshold based at least in part on at least one of an energy deposited in the subregion, a noise level associated with the baseline phase image and/or treatment phase image or the deviation between the temperature change in the generated thermal map and the predicted temperature change.

6. The system of claim 1, further comprising a medical device configured to cause the temperature change of the subregion.

7. The system of claim 6, wherein the medical device comprises an ultrasound transducer including a plurality of transducer elements, the controller being further configured to computationally predict the temperature change of the subregion using a physical model.

8. The system of claim 7, wherein the physical model is based at least in part on values of ultrasound parameters for generating a focal zone at the subregion.

9. The system of claim 8, wherein the ultrasound parameters comprise at least one of an amplitude, a frequency, a phase, a direction or an activation time associated with each of the transducer elements.

10. The system of claim 1, wherein the controller is further configured to computationally predict, without reference to the generated thermal map, the temperature change of the subregion using a physical model.

11. The system of claim 10, wherein the physical model is based at least in part on a tissue characteristic associated with at least one of the subregion or a second subregion different from the subregion.

12. The system of claim 11, wherein the controller is further configured to acquire the tissue characteristic based at least in part on imaging data acquired using the MRI unit.

13. The system of claim 11, wherein tissue characteristic comprises at least one of a type, a structure, a thickness, a density, a speed of sound, a thermal absorption coefficient, a perfusion coefficient, or a metabolic heat generation rate.

14. The system of claim 10, wherein the physical model is based on a bioheat transfer equation.

15. The system of claim 14, wherein the bioheat transfer equation includes the Pennes equation.

16. The system of claim 1, wherein the controller is further configured to predict the temperature change of the subregion using a statistical model.

17. The system of claim 16, further comprising a medical device configured to cause the temperature change of the subregion, wherein the statistical model includes historical data of the change in temperature resulting from previous activation of the medical device.

18. The system of claim 1, wherein the controller is further configured to cause the MRI unit to acquire a reference library including a plurality of baseline MR phase images of the imaging region, each corresponding to a phase background during a different stage of an anticipated motion of the imaging region.

19. The system of claim 18, wherein the controller is further configured to identify a baseline phase image in the reference library that best matches the treatment MR phase image based on similarity therebetween and generate the thermal map based at least in part on the identified best-matching baseline MR phase image.

20. A method of performing magnetic resonance (MR) thermometry, the method comprising:

acquiring at least one baseline MR phase image of an imaging region and at least one treatment MR phase image of the imaging region subsequent to a temperature change of a subregion within the imaging region;

electronically generating a thermal map pixelwise indicating the temperature change of the subregion based at least in part on a proton-resonance frequency shift of the acquired baseline phase image relative to the treatment phase image;

computationally predicting, without reference to the generated thermal map, the temperature change of the subregion based at least in part on energy deposited in the subregion during treatment; and determining whether the thermal map is inaccurate based at least in part on the temperature change of the subregion indicated by the thermal map and the predicted temperature change of the subregion, and, if so, generate a new thermal map pixelwise indicating the temperature change of the subregion based at least in part on the acquired baseline MR phase image and treatment MR phase image.

21. A system for performing magnetic resonance (MR) thermometry, the system comprising:

a magnetic resonance imaging (MRI) unit; and a controller in communication with the MRI unit and configured to:

(i) cause the MRI unit to acquire at least one baseline MR phase image of an imaging region and a plurality of treatment MR phase images of the imaging region subsequent to at least a temperature change of a subregion within the imaging region;

(ii) electronically generate a plurality of thermal maps based at least in part on proton-resonance frequency shifts of the acquired baseline MR phase relative to the treatment MR phase images, each thermal map pixelwise indicating the temperature change of the subregion associated with one of the treatment phase images; and (iii) determine whether one of the thermal maps is inaccurate based at least in part on a comparison between the temperature change associated therewith and the temperature change associated with at least another one of the thermal maps, and, if so, generate a new thermal map pixelwise indicating the temperature change of the subregion based at least in part on the acquired baseline MR phase image and treatment MR phase image.

* * * * *